(12) United States Patent
Chornenky et al.

(10) Patent No.: US 7,267,676 B2
(45) Date of Patent: Sep. 11, 2007

(54) METHOD FOR HAIR REMOVAL BY ELECTROPORATION

(75) Inventors: Victor I. Chornenky, Minnetonka, MN (US); Ali Jaafar, Eden Prairie, MN (US)

(73) Assignee: Minnesota Medical Physics LLC, Edina, MN (US)

( * ) Notice: Subject to any disclaimer, the term of this patent is extended or adjusted under 35 U.S.C. 154(b) by 0 days.

(21) Appl. No.: 11/690,175

(22) Filed: Mar. 23, 2007

(65) Prior Publication Data

US 2007/0161982 A1 Jul. 12, 2007

Related U.S. Application Data

(62) Division of application No. 10/801,783, filed on Mar. 16, 2004, now Pat. No. 7,211,083.

(60) Provisional application No. 60/454,672, filed on Mar. 17, 2003.

(51) Int. Cl.
*A61B 18/14* (2006.01)
(52) U.S. Cl. ............................. 606/44; 606/36; 606/43
(58) Field of Classification Search ................. 606/36, 606/43, 44
See application file for complete search history.

(56) References Cited

U.S. PATENT DOCUMENTS

| | | | | |
|---|---|---|---|---|
| 5,052,391 A * | 10/1991 | Silberstone et al. | .......... | 607/46 |
| 5,533,999 A * | 7/1996 | Hood et al. | ..................... | 606/5 |
| 5,983,131 A * | 11/1999 | Weaver et al. | ................ | 604/20 |
| 5,999,847 A * | 12/1999 | Elstrom | ....................... | 604/20 |
| 6,132,419 A * | 10/2000 | Hofmann | ................. | 604/890.1 |
| 6,159,163 A * | 12/2000 | Strauss et al. | ............. | 600/566 |
| 6,210,402 B1 * | 4/2001 | Olsen et al. | ................... | 606/32 |
| 6,261,831 B1 * | 7/2001 | Agee | ....................... | 435/285.2 |
| 6,326,177 B1 * | 12/2001 | Schoenbach et al. | ..... | 435/173.7 |
| 6,493,592 B1 * | 12/2002 | Leonard et al. | ............. | 607/149 |
| 6,669,691 B1 * | 12/2003 | Taimisto | ...................... | 606/41 |
| 6,697,669 B2 * | 2/2004 | Dev et al. | ..................... | 604/21 |
| 6,912,417 B1 * | 6/2005 | Bernard et al. | ............... | 604/20 |
| 2002/0010491 A1 * | 1/2002 | Schoenbach et al. | .......... | 607/2 |
| 2002/0099323 A1 * | 7/2002 | Dev et al. | ..................... | 604/21 |
| 2003/0225360 A1 * | 12/2003 | Eppstein et al. | ............. | 604/19 |
| 2005/0049541 A1 * | 3/2005 | Behar et al. | .................. | 604/20 |

\* cited by examiner

*Primary Examiner*—Michael Peffley
*Assistant Examiner*—Alex Toy
(74) *Attorney, Agent, or Firm*—Craig Gregersen

(57) ABSTRACT

The present invention provides method for removal of body hair using electroporation using an apparatus having a pulse generator capable of generating electrical pulses of the desired amplitude and duration to kill hair follicles and an applicator having a first electrode placed in contact with a hair follicle and a second electrode interacting with the first electrode to provide an electroporating field in the tissue volume surrounding a hair to be removed. The method utilize a TENS system to provide patient relief from discomfort experienced by application of the electroporation pulses.

5 Claims, 2 Drawing Sheets

METHOD FOR HAIR REMOVAL BY ELECTROPORATION

The present application claims priority from and is a divisional patent application of U.S. patent application Ser. No. 10/801,783, filed Mar. 16, 2004, now U.S. Pat. No. 7,211,083, and entitled Apparatus and Method for Hair Removal by Electroporation, the specification and drawings of which are incorporated herein in their entirety by reference, which in turn claims priority from Provisional Patent Application Ser. No. 60/454,672, filed Mar. 17, 2003, and entitled Apparatus and Method for Hair Removal by Electroporation, the specification and drawings of which are incorporated herein in their entirety by reference.

BACKGROUND OF THE INVENTION

The field of this invention relates to electrical apparatuses and methods for permanent removal of undesirable hair on human beings.

Procedures and apparatus for the removal of unwanted hair on human beings has long been known in the cosmetic art, the goal being to improve the patient's appearance. The prime objective of such procedures is the permanent removal of the hair as a result of a single application. Hair removal applications normally accomplish this objective by destroying the hair follicle from which the hair grows. To avoid unsightly scarring and to increase the patient's comfort during hair removal procedures, procedures to destroy a hair follicle have to be accomplished with a minimum amount of destruction of the tissue surrounding the follicle and a minimum level of patient discomfort and pain during and after the procedure.

For a great many years, direct current electrolysis has been used for permanent hair removal. The direct current produces a chemical reaction in and around the follicle, the main product of which is sodium hydroxide, or lye. This sodium hydroxide is an aggressive chemical that completely destroys the hair.

The main advantage of direct current electrolysis is a low rate of re-growth. Nevertheless, the method has certain disadvantages. First, direct current electrolysis requires the application of the current for a substantial period of time (one to three minutes) for each hair follicle. Also, direct current electrolysis is somewhat painful to the patient.

In recent years, a new electrolysis technique, called "thermolysis" became prevalent in this arena. Thermolysis uses a probe in the same manner as direct current electrolysis and also removes a single hair at a time. With thermolysis, however, radio frequency radiation—not direct current as in direct current electrolysis—is applied to the follicle. Over a period of several seconds the radio frequency energy thermally coagulates the follicle, thereby destroying it and preventing it from subsequently regrowing.

A disadvantage of thermolysis as a technique for hair removal is that the heating pattern is narrow. Consequently, it has been generally found that thermolysis has a low reliability factor when used on heavy hair due to the fact that heavy hair follicles are too wide for the heating pattern. The technique also has a low reliability factor when used with curly hair because the follicle itself will curl away from the probe and thereby leave hair follicle areas that have not been destroyed. Any portion of the hair follicle that has not been destroyed will be capable of re-growing hair.

Consequently, despite the prior art, a need still exists for a hair removal device that produces long-lasting results and is simple, fast and easily manipulated by the user. As disclosed herein, applicants' propose apparatus and method utilizing "electroporation" to satisfy that need.

The term electroporation (sometimes referred to hereafter as "EP") is used herein to refer to the use of a pulsed electric field to induce microscopic pores in the membranes of living cells. Living cells include a biological membrane, also commonly called a cell wall, which separates the inner volume of a cell, or cytosol, from the extracellular space, which is filled with lymph. This membrane performs several important functions, not the least of which is maintaining gradients of concentration of essential metabolic agents across the membrane. This task is performed by active protein transporters, built in the membrane and providing transport of the metabolites via controlled openings in the membrane. Inducing relatively large pores in the cell membrane by electroporation creates the opportunity for a fluid communication through the pores between the cytosol and the extracellular space that may lead to a drastic reduction of these vitally important gradients of concentrations of the metabolic agents. Uncontrolled exchange of metabolic agents, such as ions of sodium, potassium, and calcium between a living cell and the extracellular space imposes intensive biochemical stress on the cell.

When a cell is experiencing biochemical stress the major biochemical parameters of the cell are out of equilibrium and the cell cannot perform its routine functions. In an attempt to repair itself, the cell starts working in a damage control mode to restore the cell to its normal biochemical equilibrium by transporting metabolic agents or chemicals across the cell membrane into and out of the cell. The active protein transporters (or pumps), which routinely provide transport of various metabolic agents, especially proteins, across membranes, use the energy of hydrogen or sodium positive ions passing from the positive potential of the intracellular space to the negative potential of the cytosol for transport of metabolic agents into the cell, or the energy of a negative chlorine ion for transport of metabolic agents in the opposite direction out of the cell. This energy supply is provided by maintaining the potential difference across the membrane at a particular level, which, in turn, is linked to the difference in concentrations of sodium and potassium ions across the membrane. When the potential difference across the membrane is too low, thousands of the active transporters find themselves out of power and the cell finds repair difficult and in some cases unlikely if not impossible as the intracellular space is invaded by extracellular chemicals.

Invasion by high concentrations of calcium ions from the interstitial space between cells, where the calcium ion concentration is about 10,000 times higher than in the cytosol, triggers an emergency production of actin filaments across the large pores in the membrane in an attempt by the cell to bridge the edges of the pores, pull the edges together, and thereby seal the opening in the membrane. In muscle cells the calcium ion invasion may cause lethal structural damage by forcing the cell to over-contract and rupture itself.

As noted earlier, the application of a pulsed electric field can create membrane pores. Small pores in the membrane created by a relatively short electric pulse can reseal themselves spontaneously and almost instantaneously after the removal of electric field. No significant damage to the cell is done in this case. Contrary to that, larger pores may become meta-stable with very long life time and cause irreversible damage to the cell. It can be said that, depending on the number, effective diameter and lifetime of pores in the membrane, electroporation of the cell may result in significant metabolic or structural injury of the cell and/or its death. The cause of cell death after electroporation is believed to be an irreversible chemical imbalance and structural damage resulted from the fluid communication of the cytosol and the extracellular environment.

Below a certain limit of the electric field no pores are induced at all. This limit, usually referred to as the "lower EP limit" of electroporation, is different for different cells, depending, in part, on their sizes in an inverse relationship. That is, pores are induced in larger cells with smaller electric fields while smaller cells require larger electric fields. Above the lower EP limit the number of pores and their effective diameter increase with both the amplitude and duration of the electric field pulses.

Removing the electric field pulses enables the induced pores to reseal. This process of resealing of the pores and the ability of the cell to repair itself, discussed briefly above, currently is not well understood. The current understanding is that there is a significant range of electric field amplitudes and pulse durations in which cells survive electroporation and restore their viability thereafter. An electroporated cell may have open pores for as long as many minutes and still survive. The range of electric field amplitudes and pulse durations in which cells survive is successfully used in current biomedical practice for gene transfer and drug delivery inside living cells.

Nevertheless, the survivability of electroporated cells is limited. As the electric field amplitude and/or duration of pulses, increases, this limit, usually referred to as the "upper EP limit" of electroporation, is inevitably achieved. Above the upper EP limit, the number and sizes of pores in the cellular membrane become too large for a cell to survive. Multiple pulses cause approximately the same effect on the cells as one pulse with duration equal to the total duration of all applied pulses. After application of an electrical pulse above the upper electroporation limit the cell cannot repair itself by any spontaneous or biological process and dies. The upper EP limit is defined by the combinations of the amplitudes of electric field and pulse durations that cause cellular death.

The susceptibility of cells to electroporation depends on their size: the larger the cell, the lower the electric field and duration of a pulse capable of creating electropores. If cells of different sizes are exposed to the same electric field, the largest cells will have pores opened first and will die first if the electric field applied is above the upper limit of electroporation. The ability of electroporation to discriminate cells by their sizes is important feature of the phenomenon and may be used to selectively kill large cells in the human body.

The use of electroporation to kill cells of various types has been proposed in the prior art. For example, in U.S. patent application Ser. Nos. 20040019371 and 20030153960 filed by the same applicants as the present invention, the use of electroporation above the upper limit is proposed for killing fat tissue and in U.S. patent application Ser. No. 20030060856, also filed by the same applicants as the present invention, the use of electroporation above the upper limit for prostate tissue is proposed to treat benign prostatic hyperplasia. Applicants are unaware of any proposal to use electroporation as a hair removal technique.

Usually, electroporation of biological cells implies the application of high voltage pulses longer than a microsecond. This duration is stipulated by the time of relaxation of the cell membrane equal approximately 1 microsecond. In U.S. Pat. No. 6,326,177 B1 issued to Schoenbach et al. a method of electroporation employing ultrashort electric field pulses. The duration of these pulses is not enough to disrupt the cell membrane as described above, but they are capable of disruption of the subcellular structures that leads to the cell death. This method of using ultrashort pulses is proposed for use in killing cancer cells, though the patent also claims applicability to fat cells, bone cells, vascular cells, muscle cells, and cartilage cells.

One potential side effect of the use of electroporation in the removal of unwanted body hair is that some patients may experience some level of discomfort. The electroporation in-vivo of hair involves high voltage pulses applied to the skin of a patient. Delivery of such pulses, however, may result in the patient experiencing an unpleasant sensation of small, but palpable electric jolt or shock during pulsing. It would be desirable to provide relief from such sensations during a hair removal procedure using electroporation. Applicants propose providing such relief with non-invasive, non-drug apparatus and method that provide, if desired or necessary, transcutaneous electrical nerve stimulation (TENS) during the hair removal process.

TENS is one of the available non-drug mediated pain control techniques. It is based on a discovery that application of electrical current to the body can also interfere with transmission of pain signals along the nerve pathways and give patients a significant analgesic (pain relieving) effect. The Gate Control Theory of pain suggests that this effect is mediated by endogenous pain relieving chemicals, released by the body in response to the electric transcutaneous stimulation, consequently blocking the ability of the nerve to transmit pain signals. If a large nerve, responsible for transmission of perception of heat or touch, is carrying periodic signals from the endings on the skins, the Gate for the pain signals transmitted to the spinal cord via small nerves are closed and the pain is reduced.

Currently TENS is used primarily for symptomatic relief and management of chronic intractable pain or as an adjunctive treatment in the management of post-surgical or post-traumatic acute pain. TENS usually involves the application of a sequence of short electrical pulses with a relatively low repetition rate intended to affect the nervous system in such a way as to suppress the sensation of pain from acute or chronic injury. Typically, two electrodes are secured to the skin at appropriately selected locations. Mild electrical impulses are then passed into the skin through the electrodes to interact with the underlying nerves over the treatment site. As a symptomatic treatment, TENS has proven effective in the reduction of both chronic and acute pain of patients.

In summary, while the prior art teaches apparatus and methods for the removal of unwanted body hair, the prior art suffers from the disadvantages discussed above. It would be desirable to have apparatus and method that could provide hair removal without being subject to those disadvantages and that could, if desired or necessary, mitigate any discomfort created by the electroporation in-vivo procedure without resorting to pharmacological aids.

BRIEF DESCRIPTION OF THE INVENTION

An object of the current invention is to provide an apparatus and method for hair removal utilizing electroporation above the upper limit to destroy the cells comprising the hair follicle.

Another object of the current invention is to provide pain relief by TENS for hair removal procedure.

An apparatus for hair removal by electroporation may have an applicator and a high voltage pulse generator. The applicator may take the form of a hand-held device having at least two electrodes with one of electrode taking the form of a rod-like electrode and the other electrode, providing a return path for the current, taking the form of a substantially flat ring or annulus substantially surrounding the first electrode. The needle-type or center electrode rod may have a diameter at the tip of a fraction of a millimeter. In one implementation of the invention a thin needle adapted for penetration into the follicle may be used as a central electrode. The pulse-generator provides single or multiple pulses above the upper electroporation limit of the cells of a hair follicle to the applicator for application to a follicle.

Stated otherwise, the present invention has first and second electrodes configured as a first or central electrode and a second or outer electrode. The first electrode can adopt a generally rod-like form, preferably the form of a thin needle advantageously configured to engage a hair follicle, while the second electrode can adopt a configuration that circumscribes the first electrode and is preferably capable of engaging and conforming to the patient's body in the area surrounding a particular hair follicle that is to receive the electroporation treatment.

The electric pulse provided by the pulse generator to the applicator creates near the tip of the central electrode an electric field above the upper electroporation limit for the cells of the follicle. Application of a single or multiple pulses above the upper electroporation limit kills follicle cells, preferably all of them. The electrodes of the applicator are configured in such a manner that the electric field is highly concentrated near the tip of the central electrode and rapidly decreases with increasing distance from the electrode tip. Consequently and preferably, in accord with the present invention, at a short distance from the follicle the electric field drops below the upper electroporation limit and becomes safe for the surrounding cells. Thus in accordance with the current invention a highly localized effect of the electric field on the follicles is achieved, an effect that minimizes the impact of the application of the electric field pulses on the surrounding tissue.

In a method in accord with the present invention, unwanted hair is removed by providing a pulse generator and applicator having a plurality of electrodes, one being centrally disposed and the other arrayed thereeround. The central electrode is disposed in direct contact with the hair follicle and an electric pulse from the pulse generator is applied to the electrodes. In one embodiment of the present invention the duration of the pulse may fall in the range of tens of microseconds to milliseconds. In another embodiment of the invention the duration of the electric field pulses may fall in the submicrosecond region. These ultrashort pulses should have an electric field amplitude or voltage high enough to disrupt subcellular structures (lyposomes).

In another embodiment of the present invention, patient relief from discomfort from the electroporation treatment may be provided by a system providing an electroporation apparatus and a TENS apparatus. Apparatus in accord with this embodiment will have a pulse generator for the generator of high voltage pulses as previously described—an applicator with a central electroporation electrode and a first ring or annular electrode substantially disposed thereeround. The TENS apparatus will provide a TENS signal generator for providing TENS signals to the central electrode and the first ring/annular electrode substantially circumscribing the first or central electrode. In another embodiment, a second, outermost ring or annular electrode may be provided that circumscribes the first or inner ring electrode. In this case, TENS signals will be provided to the central and outermost electrodes, thus providing a larger area of coverage of the TENS electro-analgesic effect. A synchronizing circuit may be provided to synchronize the pulses provided to the electrodes by the electroporation generator and TENS generators. During a procedure with this embodiment, the applicator will be disposed with the central electrode in contact with the hair follicle and electroporation signals will be provided to desired of the outer ring electrodes and synchronized TENS signals will be provided to the central and the first or second ring electrodes to provide analgesic relief during the hair removal procedure.

The present invention, as well as its various features and advantages, will become evident to those skilled in the art when the following description of the invention is read in conjunction with the accompanying drawings as briefly described below and the appended claims. Throughout the drawings, like numerals refer to similar or identical parts.

DETAILED DESCRIPTION OF THE INVENTION

Figure 1:
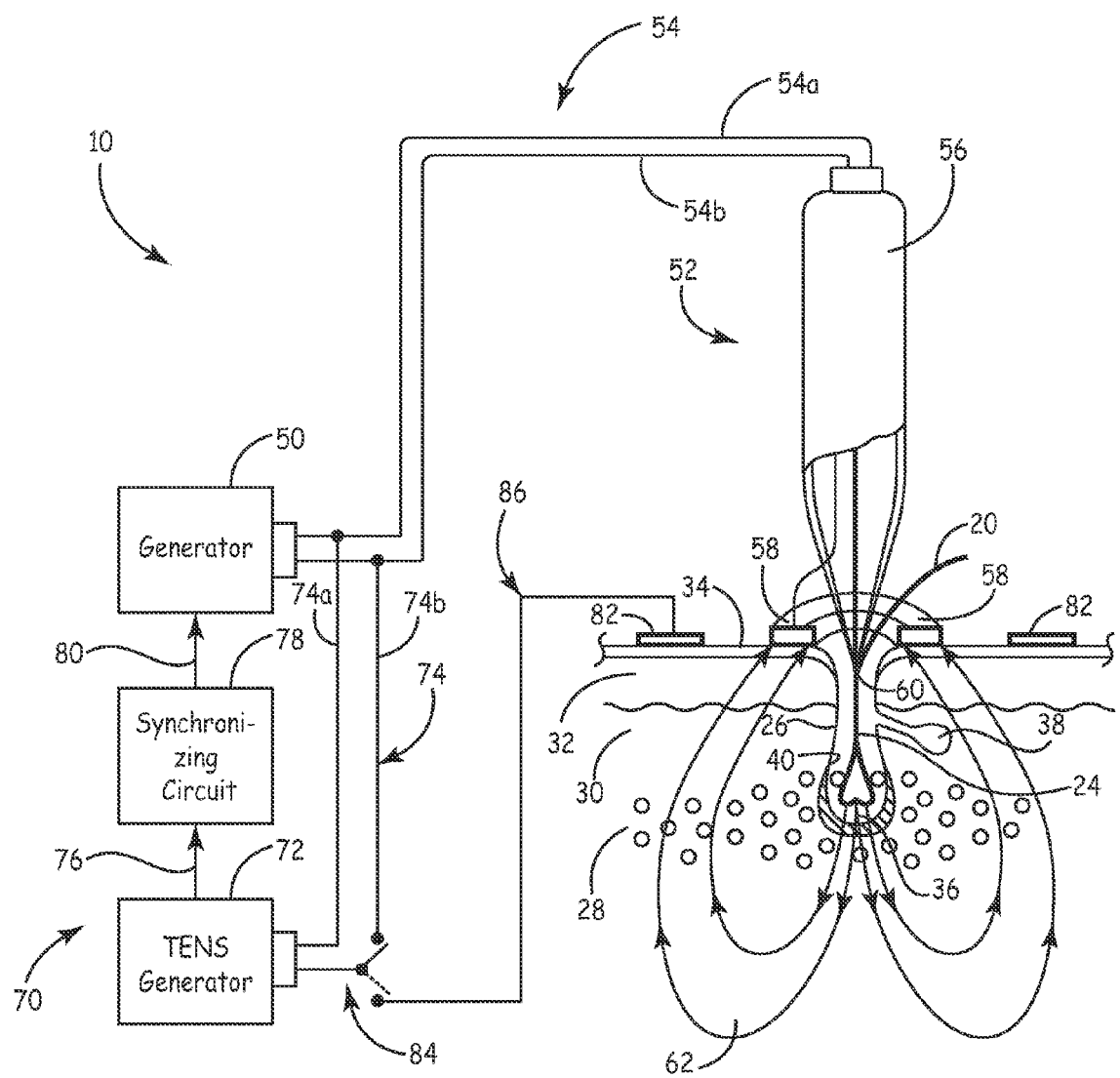
FIG. 1 illustrates an embodiment of the present invention in an operative position relative to a "patient" wherein the invention is shown in a schematic detail and the "patient" is represented by a cross-section through the patient's skin.

To understand the present invention and its operation in the removal of hair, a minimal understanding of the physical structure of the skin and structure surrounding the hair is desirable. Thus, referring to FIG. 1, an exemplary embodiment of an electroporating hair removal apparatus 10 in accord with the present invention is shown in an operative placement relative generally to a patient and more specifically to a hair 20 of the patient whose removal is desired.

Generally speaking, hair 20 includes a hair shaft 20 and a root 24. Hair 20 grows from a hair follicle 26, which extends from subcutaneous fat layer 28, through the dermis 30, the epidermis 32 and the outer surface layer of the skin, the stratum corneum, 34. The follicle 26 includes a bulb 36 from which the hair 20 grows and a sebaceous gland 38 that provides oil to lubricate the hair and skin.

Hair removal in accord with the present invention is accomplished by the application of an electroporating electric field of predetermined amplitude to preselected hairs. To determine the correct amplitude and pulse duration, consideration should be given to the electrical properties of the cells of interest, that is, the hairs and their associated cells, and how these cells, as well as surrounding cells that will experience the electric fields, respond to the application of such electric fields.

The electrical resistances of the outermost layer of the skin 34, the stratum corneum, and the inside lining 40 of the hair follicle are high and non linear. As the electric field applied to the skin increases, pores in the skin cell membranes are induced, which opens additional channels through the stratum corneum cells, dropping their resistance drops about four orders of magnitude. When a high voltage pulse is applied to the electrode contacting a hair follicle, the cell lining the inside surface of the follicle decrease its resistance first, becoming substantially more conductive. The conductive narrow channel of the follicle acts as an elongated extension of the central electrode, thus enhancing the electric field at the bottom of the follicle where the hair bulb is located. If the voltage applied to the electrode creates an electric field encompassing the bulb above the upper electroporation limit for the local cells, the cells of the bulb will die. Thus the task of the killing the cells that grow the hair will be accomplished.

It will be understood that the foregoing description of hair, skin, and subcutaneous layers is intended to be quite general in nature and that detailed descriptions of the nature, function, and interrelationship of all of the foregoing mentioned structures can be found in numerous textbooks, treatises, and medical journals the world over.

The apparatus 10 includes a high voltage pulse generator 50 and an applicator 52 connected thereto by an electrical connector 54 comprising electrical connectors 54a and 54b. Generator 50 is provided to generate and supply to applicator 52 high voltage electrical pulses in the range of 50-1000 volts. The pulse duration can be ultrashort, that is, in the range of about 0.1 nanosecond to one microsecond or they can be longer than microsecond.

Applicator 52 may take the form of a handheld device with a handle 56. Applicator 52 includes a pair of electrodes that engages the outer skin layer 34 and hair follicle 26. Thus, as illustrated, applicator 52 may include an electrode 58 electrically connected to generator 50 by connector 54b. Electrode 58 is illustrated as a substantially flat ring or annular electrode in the Figure that engages the outer skin layer 34. Applicator 52 may also include an electrode 60 electrically connected to generator 50 by connector 54b. Electrode 60 is illustrated as a rod-like electrode that engages the follicle 26. Electrode 58 substantially surrounds the rod-like electrode 60. That is, when electrode 60 engages a follicle as shown in the Figure, electrode 58 will contact an area of the patient's skin substantially, and preferably continuously, surrounding the electrode 60. As shown, the electrode 58 has a substantially flat surface for engaging the patient's skin, but other surfaces may be utilized as desired for particular applications so long as the appropriate and desired electric field can be generated in the vicinity of the hair follicle. If desired or otherwise deemed advisable, electrical contact between the electrode 60 and follicle 26 may be improved by application of the appropriate conductive gel to the electrode 60.

Application of a high voltage electroporation pulse to the electrodes 58 and 60 creates a highly concentrated electric field 62 in the general vicinity of follicle bulb 36. To kill the cells responsible for hair growth, the amplitude of the pulses, that is, the voltage, should be selected to provide an electric field 62 having a strength above the upper electroporation limit for those cells.

To significantly reduce or completely eliminate any unpleasant feelings of the patient undergoing an electroporation procedure for hair removal a TENS system may be utilized in conjunction with the electroporation apparatus to provide some degree of electro-analgesic narcosis. A TENS system 70 useful in accord with the present invention is shown in FIG. 1. TENS system 70 includes a TENS generator 72 connected via connector 74, which includes connector wires 74a and 74b connected to connectors 54a and 54b, respectively, to the output of the electroporation generator 50. Generator 72 sends electrical pulses to the electrodes 58 and 50 with a predetermined waveform providing electro-analgesia to the treated area. Connector 76 carries TENS signals from generator 72 to a synchronizing circuit 78. Circuit 78 is provided to synchronize the application of the TENS and electroporation signals so as create an analgesic effect prior to the application of the electroporation pulses. Thus, circuit 78, in response to a predetermined number of TENS pulses generates a signal delayed for approximately 0.1-1 ms after a TENS pulse to generator 50 via a connector 80 that triggers generator 50 to provide a high voltage electroporation pulse intended for electroporative killing the cells of the hair follicle. Because of refractory state induced by the last TENS pulse, the nerves in the area are unable to get excited and the electroporation pulse delivered to the treated follicle will cause significantly lower—if any—perception by the patient.

In another implementation of the invention the TENS pulses may be applied to electrode 60 and to an electrode 82 that covers a larger skin surface area than does electrode 58. This version of the apparatus may be realized by including a switch 84 as shown, which enables the operator to switch the output signal of the TENS generator from electrode 58 to electrode 82 via a connector 86. As shown, electrode 82 may also be an annular electrode with a substantially planar configuration, though it may also adopt other configurations as desired to conform to the contours of the patient's body at particular locations provided that the electro-analgesic effect of TENS therapy is not lost by such reconfigurations.

Thus, as shown, the TENS electrodes may form a different pair from the pair of electroporation electrodes of the applicator or they can be the same pair. In the first case it is preferred that the TENS electrodes are placed around the applicator's electrodes to cover a somewhat larger skin surface area than the electrodes of the electroporation applicator. In the second case the electrodes will cover of the same area, of course. In both cases the electroporation pulse is preceded by a sequence of TENS pulses providing some initial electro-analgesia, with the subsequent electroporation pulse(s) being synchronized with a TENS pulse in the sequence. EP pulses are delivered with a time delay of 1 to 1.5 ms. For the first 1.5 ms after a TENS pulse all nerves excited by a TENS pulse are in a refractory state and are unable to be excited and transmit a signal of pain or discomfort associated with the high voltage EP pulse.

Figure 2A:
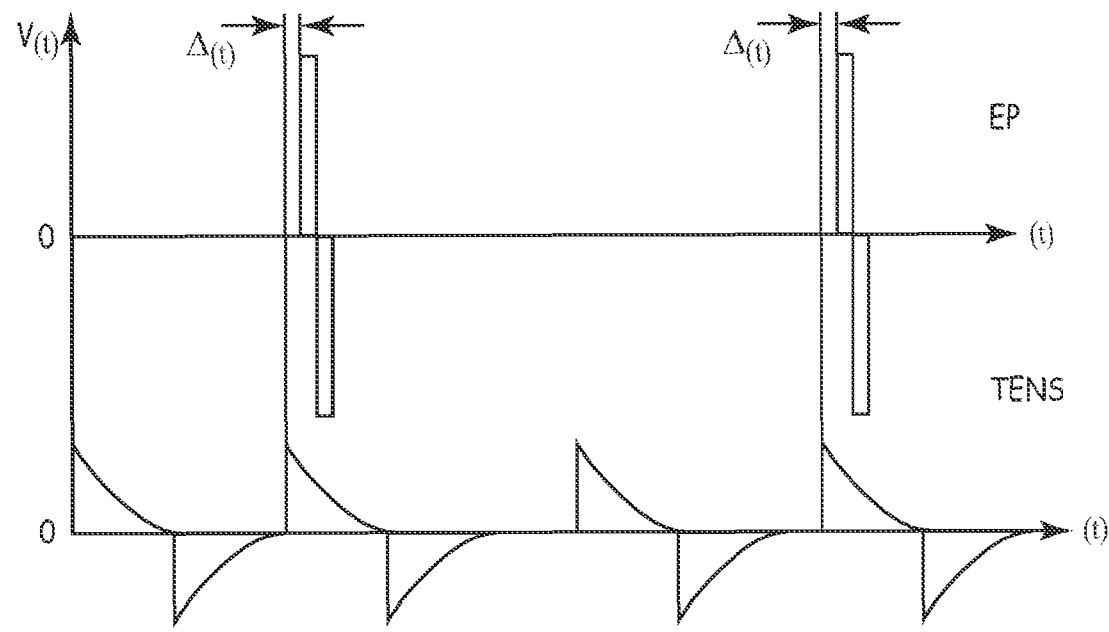
FIG. 2 shows a signal timing sequence for the application of combined electroporation and TENS pulses in accord with the present invention.
Figure 2B:
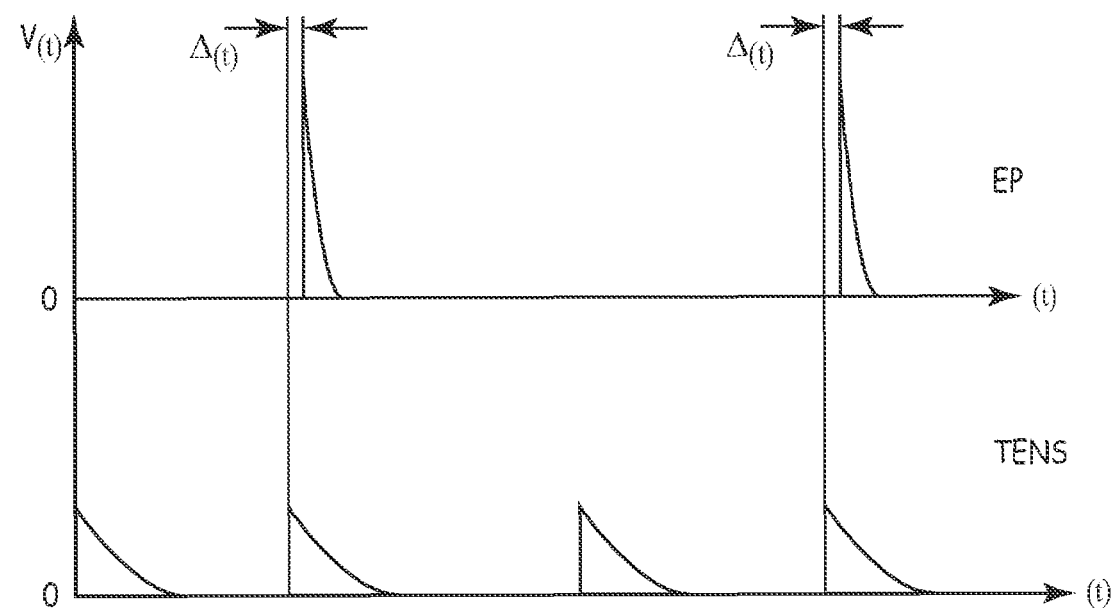

A time diagram of EP and TENS pulses is shown in FIGS. 2a and 2b. FIG. 2a shows rectangular bipolar EP pulses, which is the preferred embodiment, and FIG. 2b shows unipolar pulses for both EP and TENS pulses. Regardless of the wave form utilized, it will be observed that an EP pulse follows a TENS pulse by a time delay $\Delta t$ of approximately 1 to 1.5 ms and that the EP pulses are timed for delivery to the patient following the delivery of a plurality of TENS pulses, thus hopefully ensuring that the nerves surrounding a particular hair follicle being treated are numbed so as to reduce if not eliminate any discomfort otherwise resulting from application of the EP pulses.

A method of hair removal of present invention comprises providing a high voltage pulse generator and a hand held applicator having at least two electrodes, the geometry of which provides a highly concentrated electric field at the center electrode, applying this central electrode to a hair follicle and applying pulsed electric field to the hair follicle above the upper electroporation limit for the cells constituting the follicle and the bulb of the hair by providing high voltage electric pulses to the two electrodes.

In one to two days after an electroporation treatment as described herein, the hair will fall off. In the succeeding days, the dead cells in the follicle will be cleared by macrophages. Assuming the treatment is sufficient to kill all of the follicle cells, the hair will never grow again.

The present invention has been described in language more or less specific as to the apparatus and method features. It is to be understood, however, that the present invention is not limited to the specific features described, since the apparatus and method herein disclosed comprise exemplary forms of putting the present invention into effect. For example, while the second or outer electrode 58 has been described as being ring or disk like, the electrode could take on other forms that would conform more closely to the particular body geometry where hair is being removed than would a substantially planar disk-like electrode. The invention is, therefore, claimed in any of its forms or modifications within the proper scope of the appended claims appropriately interpreted in accordance with the doctrine of equivalency and other applicable judicial doctrines.

What is claimed is:

1. A method for removing hair from a patient, said method comprising:
    providing an electroporation system including:
        an applicator having a central electrode and an outer electrode having a substantially annular configuration; and
        a high voltage generator for providing electroporating pulses to the central and outer electrodes, the generator being electrically connected to the applicator;
    placing the central electrode in contact with a hair follicle whose removal is desired; and
    providing electroporating pulses to the electrodes for a predetermined time interval sufficient to result in the death of the hair follicle from electroporation.

2. The method of claim 1 and further including providing TENS therapy to the patient during electroporation treatment for hair removal.

3. The method of claim 2 and further including:
    providing a TENS therapy system comprising a TENS generator for supplying TENS pulses to the patient and a synchronizing circuit to synchronize the application of TENS pulses and electroporation pulses to the patient.

4. The method of claim 3 wherein the TENS therapy pulses are provided to the central and outer electrodes.

5. The method of claim 3 wherein the TENS therapy system further includes a third electrode configured to engage a larger area of patient skin surface than the outer electrode and wherein the TENS generator provides TENS therapy pulses to the central and third electrodes.

* * * * *